United States Patent
Matthys-Mark

(10) Patent No.: US 7,316,532 B2
(45) Date of Patent: Jan. 8, 2008

(54) SCREW WITH INTEGRATED SCREWDRIVER

(75) Inventor: Romano Matthys-Mark, Fideris (CH)

(73) Assignee: Synthes (U.S.A.), West Chester, PA (US)

( * ) Notice: Subject to any disclaimer, the term of this patent is extended or adjusted under 35 U.S.C. 154(b) by 0 days.

(21) Appl. No.: 11/197,717

(22) Filed: Aug. 3, 2005

(65) Prior Publication Data

US 2006/0039772 A1 Feb. 23, 2006

Related U.S. Application Data

(63) Continuation of application No. PCT/CH03/00101, filed on Feb. 12, 2003.

(51) Int. Cl.
*F16B 31/00* (2006.01)

(52) U.S. Cl. .................... 411/5; 411/3; 606/73

(58) Field of Classification Search ............ 411/1–5, 411/410, 396, 399, 412, 413, 426, 910; 606/65, 606/66, 72, 73, 104, 232
See application file for complete search history.

(56) References Cited

U.S. PATENT DOCUMENTS

| | | | |
|---|---|---|---|
| 2,699,774 A * | 1/1955 | Livingston | 606/65 |
| 5,120,168 A * | 6/1992 | Padula | 411/5 |
| 5,501,695 A * | 3/1996 | Anspach et al. | 606/232 |
| 5,653,710 A | 8/1997 | Harle | |
| 5,709,686 A | 1/1998 | Talos et al. | |
| 5,743,914 A * | 4/1998 | Skiba | 606/73 |
| 5,928,236 A * | 7/1999 | Augagneur et al. | 606/73 |
| 5,971,987 A * | 10/1999 | Huxel et al. | 606/73 |
| 6,004,349 A * | 12/1999 | Jackson | 606/61 |
| 6,056,471 A * | 5/2000 | Dinitz | 403/2 |
| 6,179,841 B1 * | 1/2001 | Jackson | 606/73 |
| 6,193,719 B1 * | 2/2001 | Gournay et al. | 606/61 |
| 6,214,012 B1 * | 4/2001 | Karpman et al. | 606/93 |
| 6,224,596 B1 * | 5/2001 | Jackson | 606/61 |
| 6,290,711 B1 * | 9/2001 | Caspari et al. | 606/232 |
| 6,623,486 B1 * | 9/2003 | Weaver et al. | 606/69 |
| 6,699,251 B1 * | 3/2004 | Venturini | 606/73 |
| 6,723,099 B1 * | 4/2004 | Goshert | 606/72 |
| 6,726,689 B2 * | 4/2004 | Jackson | 606/73 |
| 6,783,527 B2 * | 8/2004 | Drewry et al. | 606/61 |
| 6,786,907 B2 * | 9/2004 | Lange | 606/61 |
| 6,821,278 B2 * | 11/2004 | Frigg et al. | 606/69 |
| 6,875,215 B2 * | 4/2005 | Taras et al. | 606/73 |
| 6,884,244 B1 * | 4/2005 | Jackson | 606/73 |
| 6,955,677 B2 * | 10/2005 | Dahners | 606/69 |
| 6,997,927 B2 * | 2/2006 | Jackson | 606/73 |
| 7,018,379 B2 * | 3/2006 | Drewry et al. | 606/61 |
| 2002/0156476 A1 * | 10/2002 | Wilford | 606/72 |

(Continued)

FOREIGN PATENT DOCUMENTS

EP    0323429 A1    7/1989

(Continued)

*Primary Examiner*—William L. Miller
(74) *Attorney, Agent, or Firm*—Fay Kaplun & Marcin, LLP

(57) ABSTRACT

A screw with an integrated screwdriver, the screw having a screw shaft with a thread, a screw head, and a longitudinal axis, and the screwdriver being connected coaxially with the longitudinal axis over a specified breaking point with the screw head, characterized in that the screw head has an external thread.

14 Claims, 3 Drawing Sheets

U.S. PATENT DOCUMENTS

| | | | |
|---|---|---|---|
| 2003/0040751 A1* | 2/2003 | Weil et al. | 606/73 |
| 2003/0167072 A1* | 9/2003 | Oberlander | 606/232 |
| 2004/0073218 A1* | 4/2004 | Dahners | 606/69 |
| 2004/0199258 A1* | 10/2004 | Macara | 623/22.32 |
| 2004/0243129 A1* | 12/2004 | Moumene et al. | 606/73 |
| 2004/0249381 A1* | 12/2004 | Weil et al. | 606/73 |
| 2005/0080421 A1* | 4/2005 | Weaver et al. | 606/69 |
| 2005/0245933 A1* | 11/2005 | Sevrain | 606/73 |
| 2005/0251142 A1* | 11/2005 | Hoffman et al. | 606/65 |
| 2005/0267477 A1* | 12/2005 | Jackson | 606/72 |

FOREIGN PATENT DOCUMENTS

| | | |
|---|---|---|
| FR | 2721819 A1 | 1/1996 |
| FR | 2760628 A1 | 9/1998 |

* cited by examiner

SCREW WITH INTEGRATED SCREWDRIVER

CROSS-REFERENCE TO RELATED APPLICATIONS

This is a continuation of International Application No. PCT/CH2003/000101, filed on Feb. 12, 2003, the entirety of which is expressed incorporated by reference herein.

FIELD OF THE INVENTION

The invention relates to a screw with an integrated screwdriver.

BACKGROUND OF THE INVENTION

Especially in the case of screws of small dimensions, as used, for example, in osteosynthesis, the problems of securely handling, holding and guiding the screw arise. It may already turn out to be extremely difficult to take hold of smaller screws, especially in the case of exacting tasks, as encountered, for example, in bone surgery.

A further problem consists therein that, with conventional screwdrivers, it is not possible to control the torque. Special torque screwdrivers are required in order to be able to use a previously determined torque.

SUMMARY OF THE INVENTION

The invention is to provide a remedy here. It is an object of the invention to provide a screw, which can be anchored at a stable angle with a screwdriver, which is integrated over a predetermined breaking point, so that the screw can be screwed in easily and at a stable angle with a predetermined torque.

By means of the external thread, which is provided at the head of the screw and corresponds to a corresponding (circularly cylindrical or conical) internal thread in the plate borehole, it is ensured that the plate is not pressed against the bone and the screw is anchored securely and angularly stably in the plate and also remains there. This is in contrast to a smooth, conical construction of the head of the screw, for which the head is jammed tight only because of friction and thus is not held positively. The frictional connection, which is based only on the force of friction, arises due to the counterhold of the bone when the screw is tightened and has the disadvantage that it can become loose once again when the screw is stressed. When the screw is tightened, the integrated screwdriver is sheared off at the predetermined breaking point, the shear moment being defined by the dimensions selected for the predetermined breaking point.

The inventive screw with the integrated screwdriver also permits screws of very small dimensions to be held easily and, guided well, to be screwed into a borehole, such as that of a bone plate. Due to the coaxial arrangement of the integrated screwdriver and its firm connection with the head of the screw, the screw can be taken up in any position about the longitudinal axis and there is no need to take into account the position of the screwdriver.

In the case of a particular embodiment, the head of the screw expands conically in the direction of the screwdriver. This permits the head of the screw to be fixed at a stable angle in a bone plate with a corresponding conical plate borehole.

Advantageously, the thread of the shaft of the screw is constructed to be self cutting, in that a corresponding groove, which extends essentially parallel to the longitudinal axis of the screw, is provided at its free end, that is, at the tip of the screw. The inventive device is suitable especially for screws of small dimensions, typically those with a diameter of less than 2.0 mm and preferably of less than 1.0 mm.

The predetermined breaking point advantageously should have a diameter, which is larger than the diameter of the thread undercut disposed between the shaft and head of the screw.

In the case of a special embodiment, the predetermined breaking point has a diameter of 60 to 82% and preferably of 65 to 75% of the external diameter of the thread. In absolute numbers, the predetermined breaking point may have a diameter of 0.25 to 0.5 mm and preferably of 0.32 to 0.38 mm.

The screw with the integrated screwdriver may be connected over a coupling with a mechanical driving mechanism. This driving mechanism may either be a manually actuated handle or a motor-driven machine.

BRIEF DESCRIPTION OF THE DRAWINGS

The invention and further developments of the invention are explained in even greater detail in the following by means of partially diagrammatic representations of an example in the drawings.

DETAILED DESCRIPTION OF THE INVENTION

Figure 1:
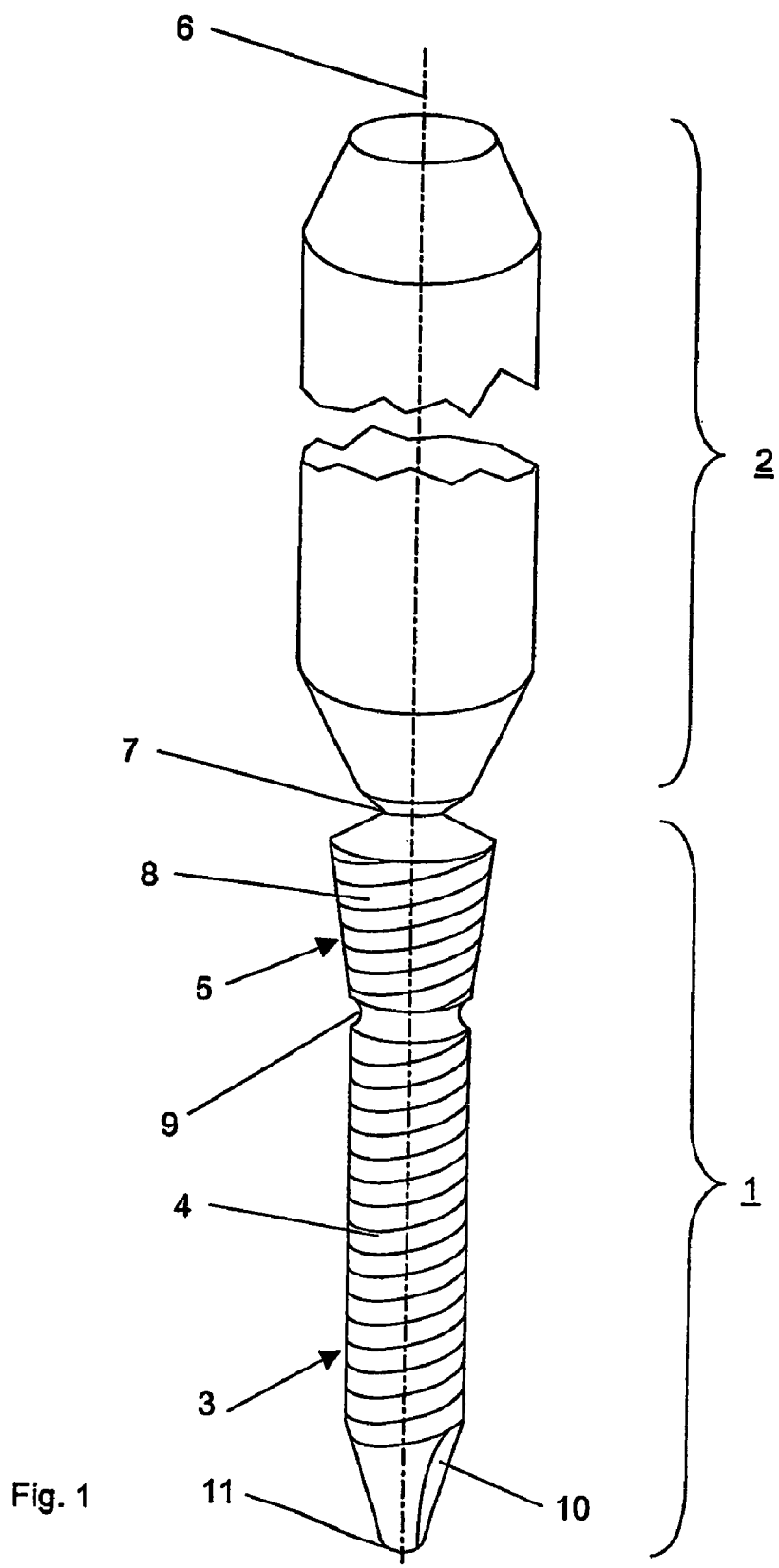
FIG. 1 shows a perspective view of the screw with the integrated screwdriver.
Figure 2:
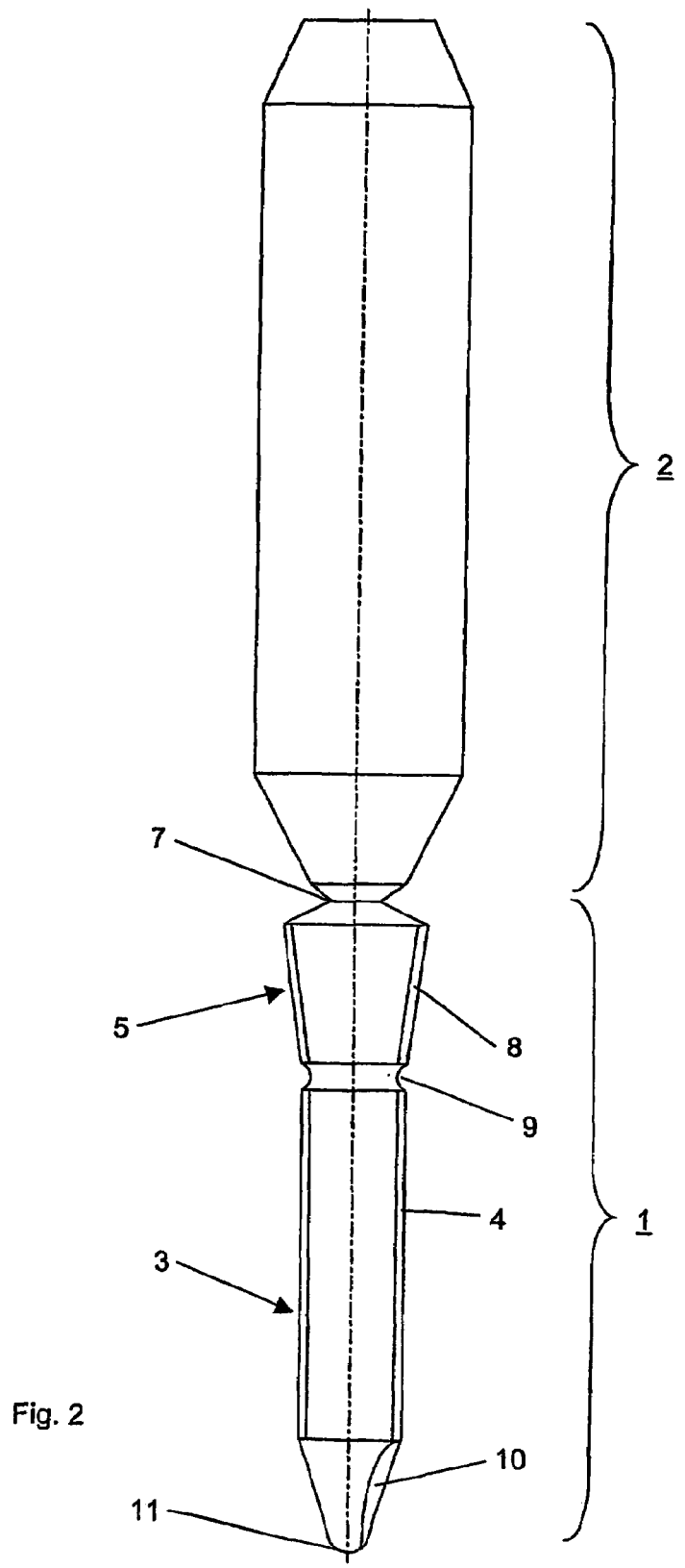
FIG. 2 shows a longitudinal section through the screw with the integrated screwdriver.

The screw 1 and the integrated screwdriver 2, shown in FIGS. 1 and 2, have a common longitudinal axis 6. The screw 1, constructed as a bone screw, has a length of 2.6 mm and a screw shaft 3, 1.3 mm long, with a thread 4 and a conical screw head 5, 1.1 mm long, with an external thread 8. Between the shaft 3 and the head 5 of the screw 1, a thread undercut 9 is disposed. The thread 4 of the shaft 3 of the screw is constructed to be self-cutting by means of a groove 10. The screwdriver 2 is 4.9 mm long and connected over a predetermined breaking point 7 coaxially with the screw head 5. The predetermined breaking point has a diameter of 0.35 mm.

Figure 3:
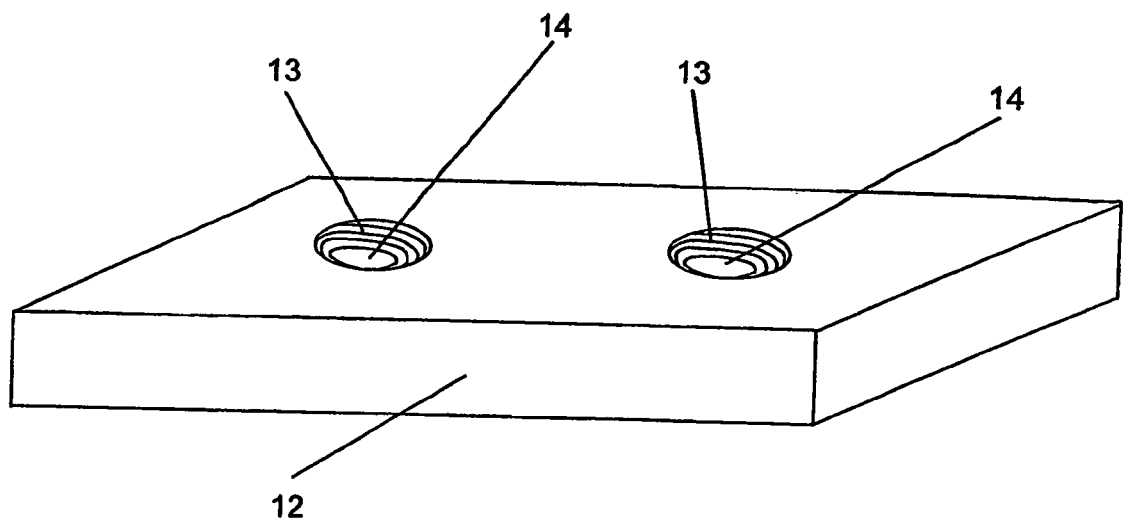
FIG. 3 shows a perspective view of a bone plate for accommodating a screw of a FIG. 1.

The screw 1 may be introduced into the plate borehole 13 of the bone plate 12 shown in FIG. 3. The internal thread 14 of the plate borehole 13, corresponding to the external thread 8 of the screw 1, brings about an angularly stable anchoring of the screw 1 with respect to the bone plate 12. The internal thread 14 and the corresponding external thread 8 may also be constructed with multiple threads, preferably with two threads.

What is claimed:

1. A tool comprising:
a screw having a threaded shaft, a threaded head having a maximum diameter, and an unthreaded portion disposed between the threaded shaft and the threaded head;
a screwdriver integrally formed with the screw; and
wherein the tool has a breaking point located between the screwdriver and the maximum diameter of the head, and wherein a diameter of the threaded shaft is greater than a diameter of the unthreaded portion.

2. The tool of claim 1, wherein the unthreaded portion is substantially smaller than the threaded shaft and the threaded head.

3. The tool of claim 1, wherein the screwdriver is associated with a driving mechanism.

4. A tool comprising:
   a screw having a threaded shaft, a threaded head, and an unthreaded portion disposed between the threaded shaft and the head;
   a screwdriver integrally formed with the screw; and
   wherein the unthreaded portion has a first diameter
   wherein the tool has a breaking point having a second diameter;
   wherein the first diameter is larger than the second diameter; and
   wherein the second diameter is from about 60 percent to about 82 percent of the first diameter, and wherein the threaded shaft has a third diameter, and wherein the first diameter is less than the third diameter.

5. The tool of claim 4, wherein the second diameter is from about 65 percent to about 75 percent of the first diameter.

6. The tool of claim 4, wherein the second diameter is from about 0.25 mm to about 0.5 mm.

7. The tool of claim 4, wherein the breaking point is disposed between the head and the screwdriver.

8. The tool of claim 4, wherein the head has a fourth diameter, and wherein the first diameter is less than the fourth diameter.

9. The tool of claim 4, wherein the unthreaded portion is an undercut.

10. The tool of claim 4, wherein the screw has a first length, wherein the screwdriver has a second length, and wherein the second length is greater than the first length.

11. The tool of claim 4, wherein the threaded shaft has a plurality of threads.

12. A fixation system comprising:
   a tool comprising:
      a screw having a threaded shaft, a threaded head having a maximum diameter, and an unthreaded portion disposed between the threaded shaft and the threaded head; and
      a screwdriver integrally formed with the screw;
      wherein the tool has a breaking point located between the screwdriver and the maximum diameter of the head; and
   a plate having at least a first fixation hole for threadedly engaging at least one of the threaded shaft and the threaded head.

13. The fixation system of claim 12, wherein the plate is a bone plate.

14. The fixation system of claim 12, wherein the screw is a bone screw.

* * * * *

UNITED STATES PATENT AND TRADEMARK OFFICE
CERTIFICATE OF CORRECTION

PATENT NO. : 7,316,532 B2 Page 1 of 1
APPLICATION NO. : 11/197717
DATED : January 8, 2008
INVENTOR(S) : Matthys-Mark It is certified that error appears in the above-identified patent and that said Letters Patent is hereby corrected as shown below:

Column 4, Line 22, claim 12:

before "." insert --, and wherein a diameter of the threaded shaft is greater than a diameter of the unthreaded portion--.

Signed and Sealed this

Third Day of June, 2008

JON W. DUDAS
*Director of the United States Patent and Trademark Office*